(12) United States Patent
Bala et al.

(10) Patent No.: US 11,948,306 B2
(45) Date of Patent: Apr. 2, 2024

(54) CURVILINEAR OBJECT SEGMENTATION (71) Applicant: Palo Alto Research Center Incorporated, Palo Alto, CA (US)

(72) Inventors: Raja Bala, Pittsford, NY (US); Xuelu Li, Santa Clara, CA (US)

(73) Assignee: XEROX CORPORATION, Norwalk, CT (US)

( * ) Notice: Subject to any disclaimer, the term of this patent is extended or adjusted under 35 U.S.C. 154(b) by 385 days.

(21) Appl. No.: 17/497,285

(22) Filed: Oct. 8, 2021

(65) Prior Publication Data

US 2023/0110806 A1     Apr. 13, 2023

(51) Int. Cl.
G06T 7/12      (2017.01)
G06N 3/08     (2023.01)
G06T 7/00     (2017.01)
G16H 30/20   (2018.01)

(52) U.S. Cl.
CPC .............. *G06T 7/12* (2017.01); *G06N 3/08* (2013.01); *G06T 7/0012* (2013.01); *G16H 30/20* (2018.01); *G06T 2207/20081* (2013.01); *G06T 2207/20084* (2013.01); *G06T 2207/30101* (2013.01)

(58) Field of Classification Search
CPC ..... G06T 7/12; G06T 7/0012; G06T 2207/20081; G06T 2207/20084; G06T 2207/30101; G06T 7/11; G06N 3/08; G06N 3/0442; G06N 3/0455; G06N 3/0464; G06N 3/09; G16H 30/20; G16H 30/40
See application file for complete search history.

(56) References Cited

U.S. PATENT DOCUMENTS 10,803,592 B2 * 10/2020 Grady ............. G06T 7/0012
11,393,229 B2 *  7/2022 Zhou .............. G06N 3/045

OTHER PUBLICATIONS

Chen et al., "Combining Fully Convolutional and Recurrent Neural Networks for 3D Biomedical Image Segmentation", arXiv:1609.01006v2, Sep. 6, 2016, 9 pages.
Cicek et al., "3D U-Net: Learning Dense Volumetric Segmentation from Sparse Annotation", arXiv 1606.06650v1, Jun. 21, 2016, 8 pages.
Cui et al., "Pulmonary Vessel Segmentation based on Orthogonal Fused U-Net++ of Chest, CT Images,". In International Conference on Medical Image Computing and Computer-Assisted Intervention, pp. 293-300, 2019.
Gur et al., "Unsupervised microvascular image segmentation using an active contours mimicking neural network", In Proceedings of the IEEE International Conference on Computer Vision, pp. 10722-10731, 2019.
Iandola, et al., "Densenet: Implementing efficient convnet descriptor pyramids," arXiv1404.1869, Apr. 7, 2014, 11 pages.
Teikari et al., "Deep learning convolutional networks for multiphoton microscopy vasculature segmentation", arXiv1606.02382, Jun. 8, 2016, 23 pages.

* cited by examiner

*Primary Examiner* — Brandon J Miller
(74) *Attorney, Agent, or Firm* — Mueting Raasch Group (57) ABSTRACT

At least one input image comprising curvilinear features is received. Latent representations of the input images are learned using a trained deep neural network. At least one boundary estimate is determined based on the latent representations. At least one segmentation estimate of the at least one input image is determined based on the latent representations. The at least one image is mapped to output segmentation maps based on the segmentation estimate and the at least one boundary estimate.

20 Claims, 7 Drawing Sheets

CURVILINEAR OBJECT SEGMENTATION

TECHNICAL FIELD

The present disclosure is directed to image processing and particularly to image segmentation.

BACKGROUND

Curvilinear objects are found in many scenes in nature, common examples including wrinkles on a human face, cracks on a road, blood vessels in the retina, and roads in a satellite image. Automatic pixel-wise detection and segmentation of curvilinear objects is thus an important computer vision task impacting a wide variety of applications.

SUMMARY

Embodiments described herein involve a method comprising receiving at least one input image comprising curvilinear features. Latent representations of the input images are learned using a trained deep neural network. At least one boundary estimate is determined based on the latent representations. At least one segmentation estimate of the at least one input image is determined based on the latent representations. The at least one image is mapped to output segmentation maps based on the segmentation estimate and the at least one boundary estimate.

A system involves a processor and a memory storing computer program instructions which when executed by the processor cause the processor to perform operations. The operations comprise receiving at least one input image comprising curvilinear features. Latent representations of the input images are learned using a trained deep neural network. At least one boundary estimate is determined based on the latent representations. At least one segmentation estimate of the at least one input image is determined based on the latent representations. The at least one image is mapped to output segmentation maps based on the segmentation estimate and the at least one boundary estimate.

Embodiments involve a non-transitory computer readable medium storing computer program instructions for object segmentation, the computer program instructions when executed by a processor cause the processor to perform operations. The operations comprise receiving at least one input image comprising curvilinear features. Latent representations of the input images are learned using a trained deep neural network. At least one boundary estimate is determined based on the latent representations. At least one segmentation estimate of the at least one input image is determined based on the latent representations. The at least one image is mapped to output segmentation maps based on the segmentation estimate and the at least one boundary estimate.

The above summary is not intended to describe each embodiment or every implementation. A more complete understanding will become apparent and appreciated by referring to the following detailed description and claims in conjunction with the accompanying drawings.

BRIEF DESCRIPTION OF THE DRAWINGS

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Image segmentation refers to grouping of parts of an image that have similar image characteristics. For example, embodiments described herein involve segmentation of curvilinear objects. Embodiments described herein generally describe the curvilinear objects being blood vessels, but it is to be understood that the curvilinear features can include any object.

The analysis of blood vessels in the human body may be useful for diagnosis, treatment planning and execution, and/or evaluation of clinical outcomes in different fields, including laryngology, neurosurgery and ophthalmology, for example. Automatic segmentation of blood vessels from image scans can support clinicians in performing these tasks. Embodiments described herein involve a deep learning technique for automatic 3D segmentation of blood vessels from 2D slice and/or 3D volumetric scans of the human body.

Figure 1:
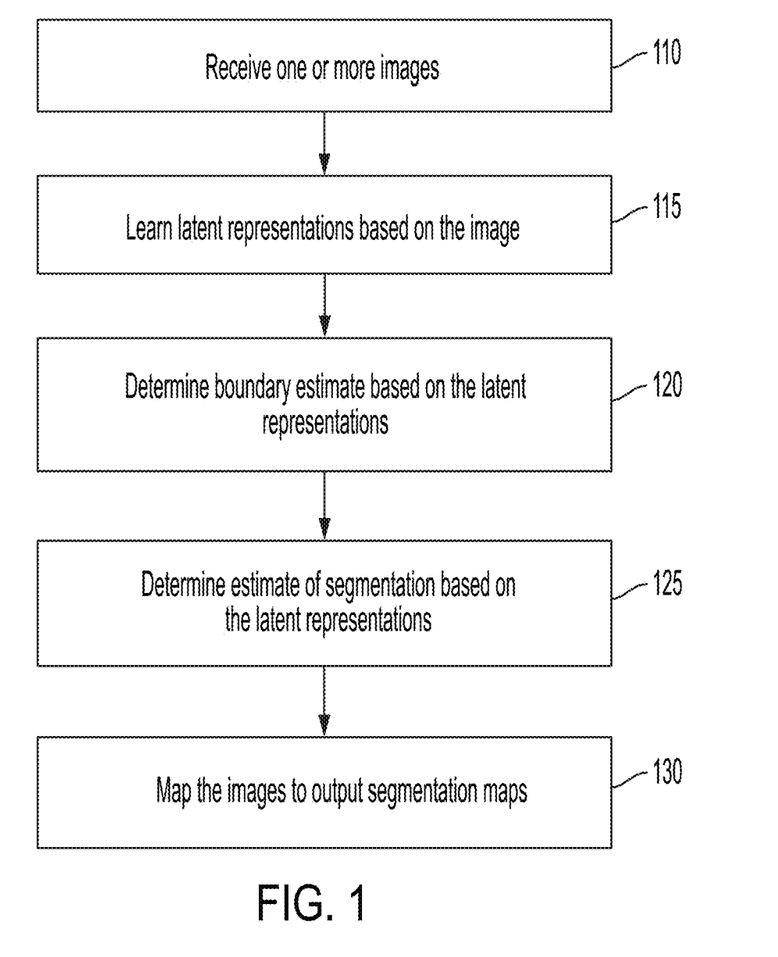
FIG. 1 illustrates a method for image segmentation in accordance with various embodiments described herein.

FIG. 1 illustrates a method for object segmentation in accordance with embodiments described herein. At least one input image comprising curvilinear features is received 110. According to various embodiments, the at least one input image comprises at least one of a 2D slice of the human body and a 3D volumetric scan of the human body. The at least one input image may comprise one or more blood vessels.

Latent representations of the input images are learned 115 using a trained deep neural network. The deep neural network may be trained using one or more images and corresponding annotated ground truth segmentation maps. At least one boundary estimate for the curvilinear features is determined 120 based on the latent representations. At least one segmentation estimate of the at least one input image is determined 125 based on the latent representations. In some cases, the at least one segmentation estimate is at least partially optimized using the at least one boundary estimate.

The at least one image is mapped 130 to output segmentation maps based on the segmentation estimate and the at least one boundary estimate. According to various embodiments, the at least one image is mapped to output segmentation maps based on a loss term encouraging one or more of homogeneity and connectedness of the curvilinear features. The at least one image may be mapped to output segmentation maps based on a network loss term that discourages short, fragmented boundaries.

According to various embodiments described herein, one or both of context and correlation are learned across the at least one input image using a recurrent neural network. In some cases, the recurrent neural network is a bidirectional long-short-term memory (LSTM) network. The at least one image may be mapped to output segmentation maps based on one or both of context and correlation.

According to various embodiments, the at least one segmentation estimate and the at least one boundary estimate are concatenated. In this case, mapping the at least one image to output segmentation maps may be done based on the concatenated at least one segmentation estimate and at least one boundary estimate.

Figure 2:
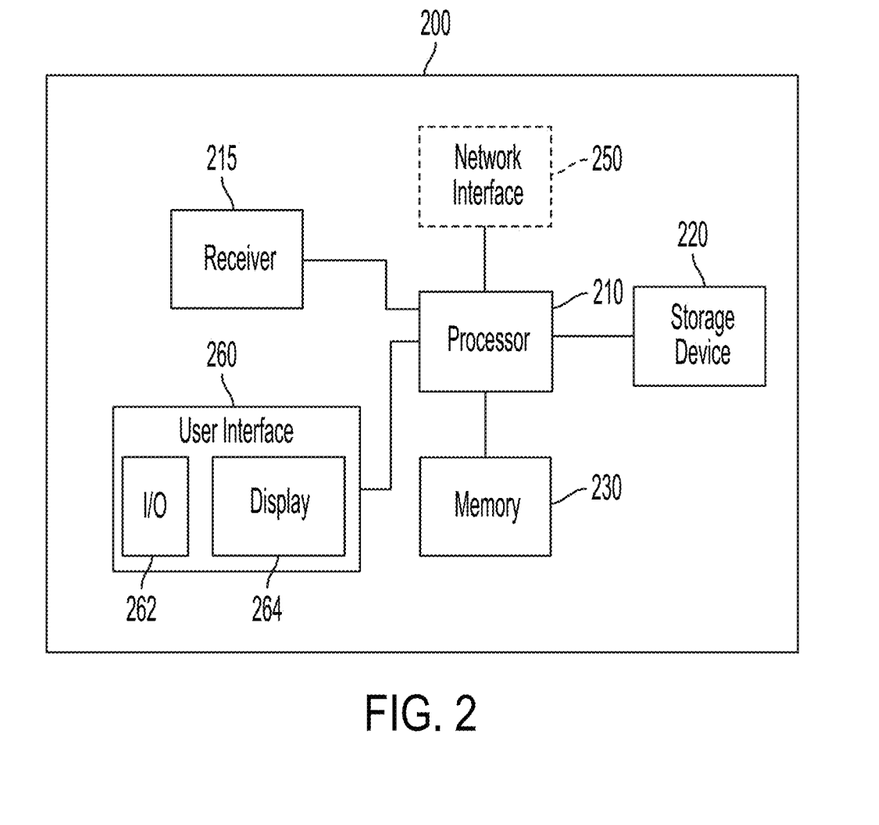
FIG. 2 shows a block diagram of a system capable of implementing embodiments described herein.

The systems described herein can be implemented by a computer using well-known computer processors, memory units, storage devices, computer software, and other components. A high-level block diagram of such a computer is illustrated in FIG. 2. Computer 200 contains a processor 210, which controls the overall operation of the computer 200 by executing computer program instructions which define such operation. It is to be understood that the processor 210 can include any type of device capable of executing instructions. For example, the processor 210 may include one or more of a central processing unit (CPU), a graphical processing unit (GPU), a field-programmable gate array (FPGA), and an application-specific integrated circuit (ASIC). The computer program instructions may be stored in a storage device 220 and loaded into memory 230 when execution of the computer program instructions is desired. Thus, the steps of the methods described herein may be defined by the computer program instructions stored in the memory 230 and controlled by the processor 210 executing the computer program instructions. The computer 200 may include one or more network interfaces 250 for communicating with other devices via a network. The computer 200 also includes a user interface 260 that enable user interaction with the computer 200. The user interface 260 may include I/O devices 262 (e.g., keyboard, mouse, speakers, buttons, etc.) to allow the user to interact with the computer. Such input/output devices 262 may be used in conjunction with a set of computer programs in accordance with embodiments described herein. The user interface may include a display 264. The computer may also include a receiver 215 configured to receive data from the user interface 260 and/or from the storage device 220. According to various embodiments, FIG. 2 is a high-level representation of possible components of a computer for illustrative purposes and the computer may contain other components.

Figure 3:
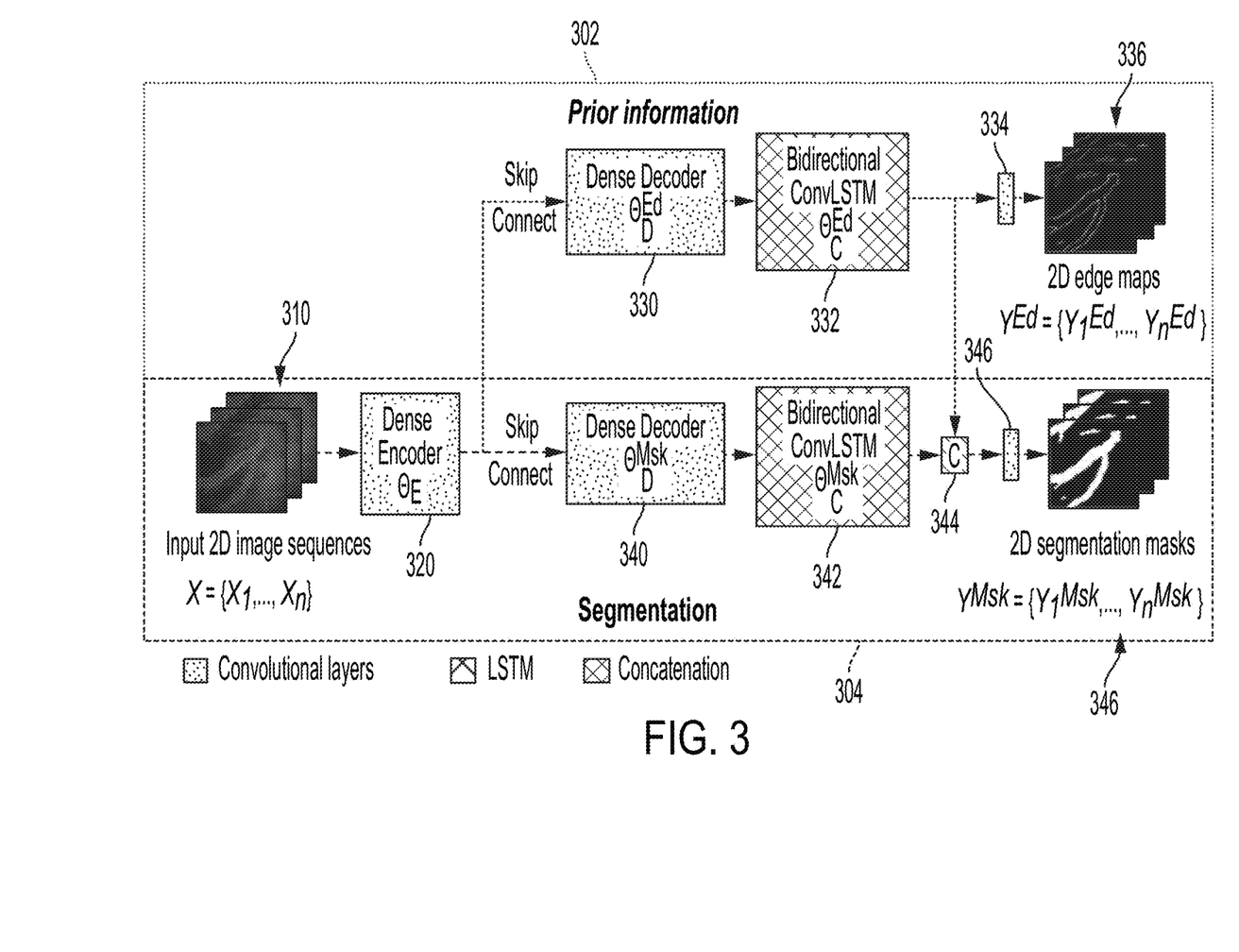
FIG. 3 illustrates a deep neural network (DNN) pathway in accordance with embodiments described herein.

FIG. 3 shows a deep neural network (DNN) pathway in accordance with embodiments described herein. The input to the DNN is a stack of 2D image slices 310 obtained from, for example, a CAT scan of a human body part that includes blood vessels of interest. The slices may be for example along the coronal, sagittal, or axial dimensions. The first block of the DNN segmentation network 304 is an encoder network 320 that learns compact latent representations from input slide data. According to some embodiments, the encoder 320 is based on the DenseNet architecture. These latent embeddings are then sent to two parallel branches. The main branch comprises a decoder network 340 (also based on DenseNet, for example) that recovers a rough estimate of the vessel segmentation map at original input resolution. Up to this point, the network learns vessel representations on a per-slice basis. Next, a recurrent neural network 342 is employed to learn context and correlation across slices. In some cases, a bidirectional long-short-term memory (LSTM) network is used as the recurrent module. A final block of convolutional layers 344 produces the output segmentation map 346 taking on values in the range 0-1, denoting the probability of a blood vessel at each pixel.

During training, input image slices 310 may be accompanied by corresponding ground truth vessel segmentation maps that have been annotated by expert clinicians. The binary cross-entropy loss between network prediction P and ground truth Y is used for training the segmentation network as shown in (1).

$$L_{CE} = -\Sigma_{ijk}(Y_{ijk}\log(P_{ijk}) + (1-Y_{ijk})\log(1-P_{ijk})) \quad (1)$$

Here, $Y_{ijk}$ denotes the ground truth vessel segmentation volume, and $P_{ijk}$ is the predicted probability that voxel ijk belongs to the blood vessel class.

According to various embodiments described herein, accurate vessel segmentation relies upon proper localization of vessel boundaries. According to embodiments described herein, an edge prior is imposed on the DNN. This task draws special attention and weighting to vessel segmentation in the vicinity of vessel boundaries. Specifically, the latent embeddings generated by the input encoder module 320 are sent to an auxiliary prior information branch 302 that is dedicated to identifying blood vessel boundaries. As with the main segmentation branch 304, the edge prediction pipeline also comprises a decoder 330, a recurrent neural network 332, and final-stage convolutional modules 332.

To train the edge prediction branch, ground truth edge maps may be computed from ground truth segmentation maps using any standard edge detection method such as the Canny Edge Detector. $L_{edge}$ may be defined as the binary cross-entropy loss (same form as (1)) for training the edge prediction branch. Note that since both the segmentation and edge prediction branches share a common encoder 320, they are trained in a joint fashion.

Figure 4A:
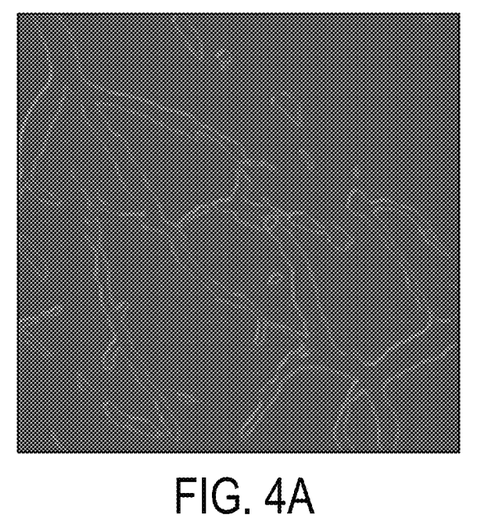
FIGS. 4A and 4B shows two exemplary feature maps brought from the edge branch to the segmentation branch in accordance with embodiments described herein.
Figure 4B:
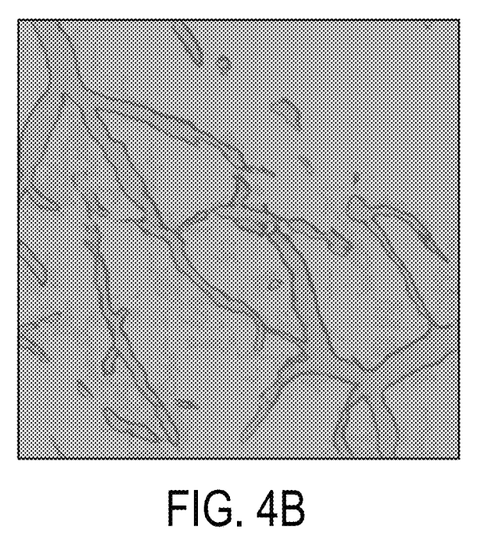

To further enhance the impact of the edge prior, the penultimate feature maps learned from the recurrent neural network 332 in the edge prediction branch 302 are concatenated 344 to feature maps learned from the recurrent neural network 342 in the main segmentation branch 304. FIGS. 4A and 4B shows two exemplary feature maps brought from the edge branch to the segmentation branch in accordance with embodiments described herein. It can be observed that these feature maps offer emphasis to vessel boundaries in the segmentation process.

Figure 5:
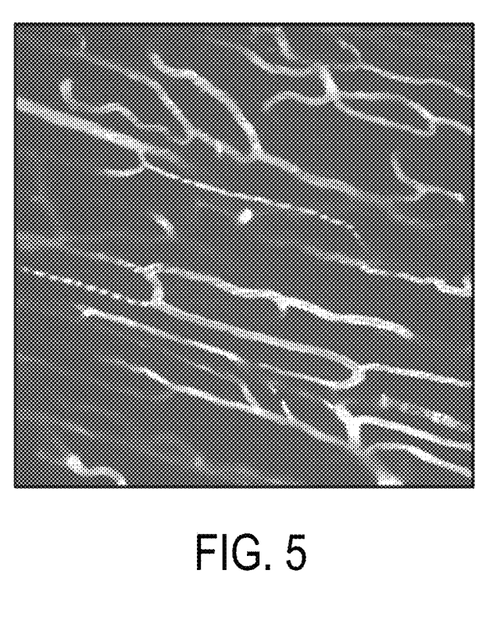
FIG. 5 illustrates an input image slice showing blood in vessels highlighted by biomarkers, resulting in locally homogeneous vessel maps in accordance with embodiments described herein.

According to various embodiments described herein, a loss term is introduced to the DNN objective for encouraging local in-vessel homogeneity and/or connectedness. The loss term may be based on the observation that biomarkers used during blood vessel imaging result in regions with blood flow being highlighted and locally homogenous. FIG. 5 illustrates an input image slice showing blood in vessels highlighted by biomarkers, resulting in locally homogeneous vessel maps in accordance with embodiments described herein.

The loss may be defined as:

$$L_{contour} = \alpha \sum_{i,j,k} P \circ \left| V - \frac{\sum_{i,j,k}(P \circ V)}{\sum_{i,j,k} P} \right| + \beta \sum_{I,J,K}(1-P) \circ \left| V - \frac{\sum_{i,j,k}(1-P) \circ V}{\sum_{i,j,k}(1-P)} \right| \quad (2)$$

Here, P is the network prediction and V denotes the input voxel value. The first term measures variation in input voxel values within the blood vessel region, while the second term measures variations in non-vessel regions. Essentially, this loss term encourages the vessel segmentation map to minimize variance both within and outside blood vessels. To encourage local homogeneity, (2) is computed over small patches within each image slice, and then summed over each slice.

According to embodiments described herein, a regularizer is introduced in the network loss as shown in (3). The regularizer may discourage short, fragmented vessel boundaries. This term may offer robustness to spurious noise and false positives.

$$L_{robust} = \sum_{i,j,k} |P_e| \quad (3)$$

The overall network loss is given by:

$$L = \lambda_1 L_{CE} + \lambda_2 L_{edge} + \lambda_3 L_{contour} + \lambda_4 L_{robust} \quad (4)$$

EXAMPLES

The proposed method was demonstrated on the VesselNN dataset which comprises 12 3D CT-scans of cortex and tumor vascular volumes from mice. In the baseline training scenario, 10 images were used for training and 2 for testing. In a low training scenario, 8 images were used for training, and 2 for testing. Images were divided into 235 512×512 patches, thus the number of training and test patches was 185 and 50 respectively.

Table 1 shows an ablation study to demonstrate the effect of various novel elements introduced one by one into the deep network. Comparison of the two training scenarios shows that the performance advantage of the proposed invention is further amplified when the training dataset is small. Table 2 shows performance of the proposed approach against other methods, all of which also employ deep learning. Comparison of the two training scenarios shows that the performance advantage of embodiments described herein is further amplified when the training dataset is small.

TABLE 1

Performance comparison w.r.t. different network architectures

|  | DICE | mIOU |
|---|---|---|
| DenseUnet | 0.762 | 0.798 |
| DenseUnet + BICLSTM$_{seg}$(SegBranch) | 0.766 | 0.800 |
| SegBranch + Edge(2D) | 0.772 | 0.804 |
| SegBranch + Edge + BICLSTM$_{edg}$(EdgeBranch) | 0.772 | 0.805 |
| SegBranch + EdgeBranch + Concatenation | 0.780 | 0.811 |

TABLE 2

Performance comparison w.r.t. different training size

|  |  | DICE | mIOU | time(s) | time/voxel (1e–6s) |
|---|---|---|---|---|---|
| low training | 3D-Unet (MICCAI 2016) [4] | 0.679 | 0.688 | 31.20 | — |
|  | UMIS (ICCV 2019) [1] | 0.527 | 0.665 | 138.56 | — |
|  | Proposed methods w/o L$_c$ and L$_r$ | 0.761 | 0.796 | 6.89 | — |
|  | Proposed methods w/o L$_c$ | 0.763 | 0.800 | 6.55 | — |
|  | Proposed method | 0.773 | 0.806 | 5.82 | — |

TABLE 2-continued

Performance comparison w.r.t. different training size

|  |  | DICE | mIOU | time(s) | time/voxel (1e–6s) |
|---|---|---|---|---|---|
| high training | 3D-Unet (MICCAI 2016) | 0.740 | 0.778 | 28.00 | 4.27 |
|  | UMIS (ICCV 2019) | 0.776 | 0.760 | 139.00 | 21.21 |
|  | Proposed methods w/o L$_c$ and L$_r$ | 0.780 | 0.811 | 6.00 | 0.92 |
|  | Proposed methods w/o L$_c$ | 0.781 | 0.812 | 6.21 | 0.93 |
|  | Proposed method | 0.785 | 0.817 | 6.85 | 1.05 |

Figure 6A:
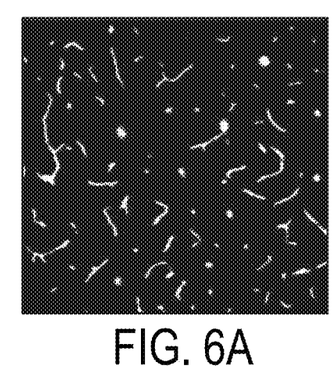
FIGS. 6A-6F shows visualizations of the network predictions of different techniques in accordance with embodiments described herein.
Figure 6B:
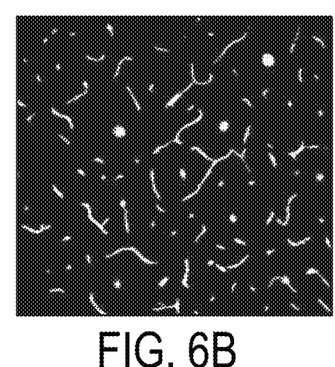
Figure 6C:
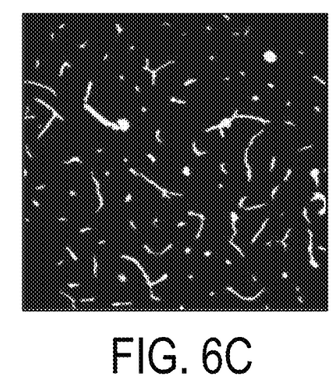
Figure 6D:
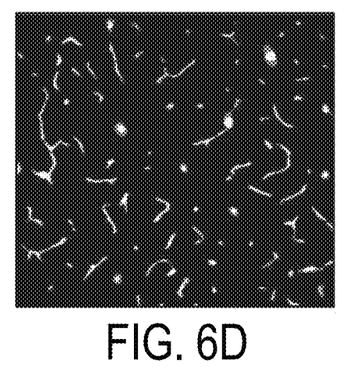
Figure 6E:
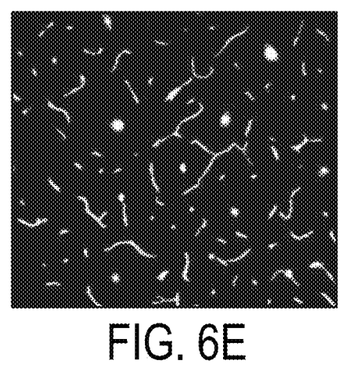
Figure 6F:
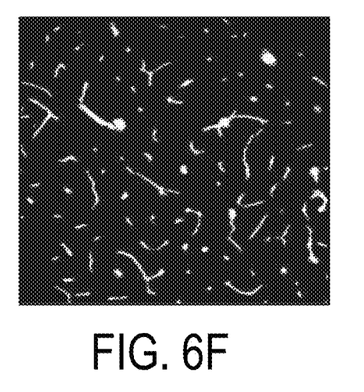

FIGS. 6A-6F shows visualizations of the network predictions of different techniques in accordance with embodiments described herein. Specifically, FIGS. 6A-6C illustrates network predications using techniques described herein. FIGS. 6D-6F shows network predications using other techniques. As can be observed, FIGS. 6A-6C show significantly fewer false negatives (i.e., missed detections when compared to the results of the techniques shown in FIGS. 6D-6F.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

The various embodiments described above may be implemented using circuitry and/or software modules that interact to provide particular results. One of skill in the computing arts can readily implement such described functionality, either at a modular level or as a whole, using knowledge generally known in the art. For example, the flowcharts illustrated herein may be used to create computer-readable instructions/code for execution by a processor. Such instructions may be stored on a computer-readable medium and transferred to the processor for execution as is known in the art.

The foregoing description of the example embodiments have been presented for the purposes of illustration and description. It is not intended to be exhaustive or to limit the inventive concepts to the precise form disclosed. Many modifications and variations are possible in light of the above teachings. Any or all features of the disclosed embodiments can be applied individually or in any combination, not meant to be limiting but purely illustrative. It is intended that the scope be limited by the claims appended herein and not with the detailed description.

What is claimed is:

1. A method for object segmentation, comprising: receiving at least one input image comprising curvilinear features; learning latent representations of the input images using a trained deep neural network; determining at least one boundary estimate based on the latent representations; determining at least one segmentation estimate of the at least one input image based on the latent representations; and mapping, using a processor, the at least one image to output segmentation maps based on the segmentation estimate and the at least one boundary estimate.

2. The method of claim 1, wherein the at least one input image comprises at least one of a 2D slice of the human body and a 3D volumetric scan of the human body.

3. The method of claim 1, wherein the at least one input image comprises one or more blood vessels.

4. The method of claim 1, further comprising learning one or both of context and correlation across the at least one input image using a recurrent neural network; and
mapping the at least one image to output segmentation maps based on one or both of context and correlation.

5. The method of claim 4, wherein the recurrent neural network is a bidirectional long-short-term memory (LSTM) network.

6. The method of claim 1, further comprising concatenating the at least one segmentation estimate and the at least one boundary estimate; and
mapping the at least one image to output segmentation maps based on the concatenated at least one segmentation estimate and at least one boundary estimate.

7. The method of claim 1, wherein mapping the at least one image to output segmentation maps comprises mapping the at least one image to output segmentation maps based on a loss term encouraging one or more of homogeneity and connectedness of the curvilinear features.

8. The method of claim 1, wherein mapping the at least one image to output segmentation maps comprises mapping the at least one image to output segmentation maps based on a network loss term that discourages short, fragmented boundaries.

9. The method of claim 1 wherein the deep neural network is trained using one or more images and corresponding annotated ground truth segmentation maps.

10. A system for object segmentation, comprising:
a processor; and
a memory storing computer program instructions which when executed by the processor cause the processor to perform operations comprising:
receiving at least one input image comprising curvilinear features;
learning latent representations of the input images using a trained deep neural network;
determining at least one boundary estimate based on the latent representations;
determining at least one segmentation estimate of the at least one input image based on the latent representations; and
mapping the at least one image to output segmentation maps based on the segmentation estimate and the at least one boundary estimate.

11. The system of claim 10, wherein the at least one input image comprises at least one of a 2D slice of the human body and a 3D volumetric scan of the human body.

12. The system of claim 10, wherein the at least one input image comprises one or more blood vessels.

13. The system of claim 10, further comprising learning one or both of context and correlation across the at least one input image using a recurrent neural network; and
mapping the at least one image to output segmentation maps based on one or both of context and correlation.

14. The system of claim 13, wherein the recurrent neural network is a bidirectional long-short-term memory (LSTM) network.

15. The system of claim 10, further comprising concatenating the at least one segmentation estimate and the at least one boundary estimate; and
mapping the at least one image to output segmentation maps based on the concatenated at least one segmentation estimate and at least one boundary estimate.

16. The system of claim 10, wherein mapping the at least one image to output segmentation maps comprises mapping the at least one image to output segmentation maps based on a loss term encouraging one or more of homogeneity and connectedness of the curvilinear features.

17. The system of claim 10, wherein mapping the at least one image to output segmentation maps comprises mapping the at least one image to output segmentation maps based on a network loss term that discourages short, fragmented boundaries.

18. The system of claim 10, wherein the deep neural network is trained using one or more images and corresponding annotated ground truth segmentation maps.

19. A non-transitory computer readable medium storing computer program instructions for object segmentation, the computer program instructions when executed by a processor cause the processor to perform operations comprising:
receiving at least one input image comprising curvilinear features;
learning latent representations of the input images using a trained deep neural network;
determining at least one boundary estimate based on the latent representations;
determining at least one segmentation estimate of the at least one input image based on the latent representations; and
mapping the at least one image to output segmentation maps based on the segmentation estimate and the at least one boundary estimate.

20. The non-transitory computer readable medium of claim 19, wherein the at least one input image comprises at least one of a 2D slice of the human body and a 3D volumetric scan of the human body.

* * * * *